United States Patent
Kashiwagi et al.

(10) Patent No.: US 11,840,542 B2
(45) Date of Patent: Dec. 12, 2023

(54) METHOD FOR PRODUCING CYCLIC ENOL ETHER COMPOUND

(71) Applicant: Kao Corporation, Tokyo (JP)

(72) Inventors: Yuki Kashiwagi, Wakayama (JP); Daichi Sakoda, Wakayama (JP)

(73) Assignee: Kao Corporation, Tokyo (JP)

( * ) Notice: Subject to any disclaimer, the term of this patent is extended or adjusted under 35 U.S.C. 154(b) by 461 days.

(21) Appl. No.: 17/280,680

(22) PCT Filed: Sep. 20, 2019

(86) PCT No.: PCT/JP2019/036991
§ 371 (c)(1),
(2) Date: Mar. 26, 2021

(87) PCT Pub. No.: WO2020/066898
PCT Pub. Date: Apr. 2, 2020

(65) Prior Publication Data
US 2022/0119404 A1    Apr. 21, 2022

(30) Foreign Application Priority Data
Sep. 28, 2018    (JP) ................. 2018-183605

(51) Int. Cl.
C07D 493/08    (2006.01)
B01J 21/06    (2006.01)
B01J 31/14    (2006.01)
C07C 45/51    (2006.01)

(52) U.S. Cl.
CPC .......... C07D 493/08 (2013.01); B01J 21/066 (2013.01); B01J 31/143 (2013.01); *B01J 2531/31* (2013.01)

(58) Field of Classification Search
CPC .... C07D 493/08; C07C 45/513; B01J 21/066; B01J 31/143; B01J 2531/13
See application file for complete search history.

(56) References Cited

U.S. PATENT DOCUMENTS

| | | | |
|---|---|---|---|
| 4,335,262 A | 6/1982 | Schulte-Elte et al. | |
| 4,480,107 A | 10/1984 | Schulte-Elte et al. | |
| 2010/0016308 A1 | 1/2010 | Burkamp et al. | |
| 2012/0088935 A1 | 4/2012 | Schelper et al. | |
| 2016/0031783 A1 | 2/2016 | Micoine et al. | |
| 2017/0362153 A1 | 12/2017 | Tanino et al. | |
| 2018/0346478 A1 | 12/2018 | Werner et al. | |

FOREIGN PATENT DOCUMENTS

| | | | |
|---|---|---|---|
| CN | 107001214 A | 8/2017 | |
| CN | 108290901 A | 7/2018 | |
| DE | 29 16 418 A1 | 11/1980 | |
| DE | 197 02 279 A1 | 7/1998 | |
| FR | 2 645 530 A1 | 10/1990 | |
| GB | 1205047 A | 9/1970 | |
| GB | 2 125 397 A | 3/1984 | |
| JP | 51-29147 A | 8/1976 | |
| JP | 56-46881 A | 4/1981 | |
| JP | 63-2946 A | 1/1988 | |
| JP | 2002-105010 A | 4/2002 | |
| JP | 2009-515864 A | 4/2009 | |
| JP | 2010-95447 A | 4/2010 | |
| JP | 2014-500237 A | 1/2014 | |
| JP | 2015-533799 A | 11/2015 | |
| JP | 2016-34937 A | 3/2016 | |
| JP | 2016-124867 A | 7/2016 | |
| JP | 2017-505835 A1 | 2/2017 | |
| JP | 2017-122101 A | 7/2017 | |
| JP | 7074869 B2 | 5/2022 | |
| WO | WO 2011/073843 A1 | 6/2011 | |
| WO | WO2012/045786 A | 4/2012 | |

(Continued)

OTHER PUBLICATIONS

Lutz, R.P., "Catalysis of the Cope and Claisen Rearrangements", Chemical Reviews, vol. 84, No. 3, Jun. 1984, 43 pages.

(Continued)

*Primary Examiner* — Sikarl A Witherspoon
(74) *Attorney, Agent, or Firm* — Oblon, McClelland, Maier & Neustadt, L.L.P.

(57) ABSTRACT

Provided is a one-step method for producing an enol ether using a diketone of a macrocyclic compound as a starting material. A method for producing a compound represented by general formula (I) includes reacting a compound represented by general formula (II) in the presence of a metal catalyst containing at least one metal element selected from the group consisting of magnesium, aluminum, zirconium, titanium, and samarium, and an alcohol containing at least one selected from the group consisting of a primary alcohol and a secondary alcohol to obtain the compound represented by general formula (I).

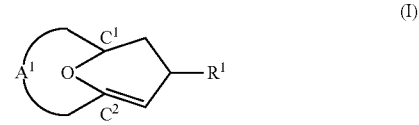

(I)

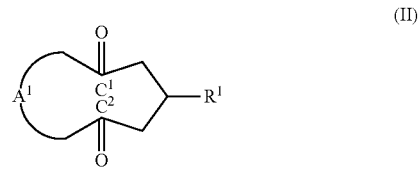

(II)

13 Claims, No Drawings

(56) References Cited

FOREIGN PATENT DOCUMENTS

| WO | WO 2015/036402 A1 | 3/2015 |
|---|---|---|
| WO | WO 2015/107017 A1 | 7/2015 |
| WO | WO 2017/089327 A1 | 6/2017 |
| WO | WO 2018/011386 A1 | 1/2018 |
| WO | WO 2019/086207 A1 | 5/2019 |

OTHER PUBLICATIONS

Israeli Office Action dated Oct. 6, 2022, in corresponding Israeli Patent Application No. 286361, 6 pages.
Ohloff, G., Becker, J. and Schulte-Elte, K.H. (1967), "Synthese von Exalton und racemischem Muscon aus Cyclododecanon" Voriaeufige Mitteilung. HCA, 50: 705-708.
Knopft, O., and J. Kuhne, "New Practical Synthesis of the Exceptional Musk Odorants (R)-Muscone and (R,Z)-5-Muscerone". Chimia, vol. 62. No. 6, Jun. 2008, p. 489-492, doi: 10.2533/chimia.2008.489.
Fehr, C., Galindo, J. and Etter, O. (2004), "An Efficient Enantioselective Synthesis of (+)-(R,Z)-5-Muscenone and (−)-(R)-Muscone—An Example of a Kinetic Resolution and Enantioconvergent Transformation", Eur. J. Org. Chem., 2004: 1953-1957.
Office Action dated Apr. 14, 2022 in co-pending U.S. Appl. No. 17/440,564, 13 pages.
Extended European Search Report dated May 20, 2022, in corresponding European Patent Application No. 19866843.6, 7 pages.
International Search Report dated Jun. 9, 2020 in PCT/JP2020/011667, 4 pages.
Rinaldo Gardi, et al., "Alkylation of Steroids by the Claisen Rearrangement of Allyl Ethers. II. Rearrangement of 17-oxo Steroid Enol Ethers" Gazzetta Chimica Italiana, vol. 95, No. 4, 1965, pp. 351-367.
"Acetal" The Chemical Society of Japan, 1992, pp. 245-258, (with English Translation).
Dubs, Paul, et al., "Novel Synthesis of a [10] (2,6) Pyridinophane, a Structural Isomer of Muscopyridine" J.C.S. Chem. Comm., 1976, p. 1021.
Ronald A. Wohl, "A Convenient One-Step Procedure for the Synthesis of Cyclic Enol Ethers. The Preparation of 1-Methoxy-1-Cycloalkenes" Syntheses, Jan. 1974; pp. 38-40.
Valentin Rautenstrauch, et al., "92. A Short Synthesis of (±)-Muscone" Helvetica Chimica Acta, vol. 73, 1990, pp. 896-901.
Masaharu Sugiura, et al., "Regiochemical Control in the Pd(II)-Catalyzed Claisen Rearrangement via In Situ Enol Ether Exchange" Tetrahedron Letters, vol. 37, No. 44, 1996, pp. 7991-7994.
Cresson, P., et al., "α-alkylation of lactams by Claisen rearrangement of 0-unsaturated enolates" C.R. Acad. SC, Serie C, vol. 275, 1972, pp. 1299-1300.
Database Casreact, AN 159:515223, Retrieved from STN international [online], 2007, 1 page.
A. Kasai, et al., "On Steroids. CXXXVII. Preparation of Some Cyclic Steroidal Ethers" Collection Czechoslov. Chem. Commun. vol. 34, 1969, pp. 3479-3496.
W. L. Howard, et al., "Working with Hazardous Chemicals" Organic Synthesis, vol. 5, 1973, 3 pages.
Horacio Mansilla, et al., "Iron(III) Tosylate in the Preparation of Dimethyl and Diethyl Acetals from Ketones and β-Keto Enol Ethers from Cyclic β-Diketones" Synthetic Communications, vol. 38, 2008, pp. 2607-2618 and cover page.
Alexander O. Terent'ev, et al., "New Transformation of Cycloalkanone Acetals by Peracids α,107 -Dicarboxylic Acids Synthesis" Central European Journal of Chemistry, vol. 3, 2005, pp. 417-431.
G. Cardinale, et al., "Bifunctional Compounds from Reactions of Alkoxy Hydroperoxides with Metal Salts" Tetrahedron, vol. 41, No. 24, 1985. pp. 6051-6054.
G. William Daub, et al., "Ketal Claisen Rearrangement of Simple Aliphatic Ketals" J. Org. Chem. vol. 48, No. 22, 1983, pp. 3876-3883.
Raucher, Stanley, et al., "Indole Alkaloid Synthesis via Claisen Rearrangement. Total Synthesis of Secodine" J. Am. Chem. Soc., vol. 103, No. 9, 1981, pp. 2419-2421.
G. William Daub, et al., "The Stereoselectivity of Ketal Claisen Rearrangements with Ketals of Simple Cyclic Ketones" Tetrahedron Letters, vol. 27, No. 52, 1986, pp. 6311-6314.
International Search report dated Dec. 10, 2019 in PCT/JP2019/036991 filed Sep. 20, 2019, 2 pages.
Rohanna, J., et al., "Olefinic-Lactone Cyclizations to Marcocycles", Organic Letters, vol. 11, No. 2, 2009, pp. 493-495.
JP Office Action (Notification of Reasons for Refusal) dated Oct. 5, 2021, in corresponding Japanese Patent Application No. 2020-549124 (with English translation).
JP Decision to Grant a Patent dated May 10, 2022, in corresponding Japanese Patent Application No. 2020-549124 (with English translation).
U.S. Pat. No. 10,087,129 B2, Oct. 2, 2018, Kenji Tanino, et al.

METHOD FOR PRODUCING CYCLIC ENOL ETHER COMPOUND

TECHNICAL FIELD

The present invention relates to a method for producing a cyclic enol ether compound represented by general formula (I).

BACKGROUND ART

Macrocyclic compounds are known to have activities useful in the fields such as medicaments, fragrances, and agrochemicals. Muscenone, which is one of macrocyclic ketones, is a fragrance material that is excellent in biodegradability and fragrance retention and has an elegant feel. To meet the recent increasing need for easily biodegradable synthetic musk materials, the development of safe and highly efficient production methods is demanded.

[Chemical Formula 1]

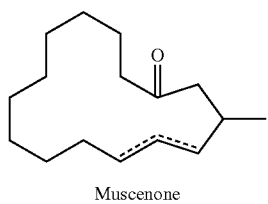

Muscenone

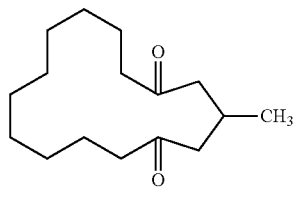

3-Methyl-cyclopentadecan-1,5-dione

Muscenone can be obtained by treating, with a strong acid, hydroxyketone 5-hydroxy-3-methylcyclopentadecan-1-one or an enol ether (i.e., 14-methyl-16-oxabicyclo[10.3.1]hexadec-12-ene), both of which are derived from 3-methyl-cyclopentadecan-1,5-dione (diketone). Several methods are known as the derivation method. For example, 3-methyl-cyclopentadecan-1,5-dione (diketone) is partially reduced to a monool or lactol and then dehydrated to muscenone. The partial reduction is performed, for example, by hydrogenation in the presence of a transition metal catalyst or by using a metal hydride.

[Chemical Formula 2]

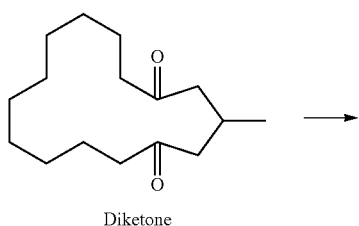

Diketone

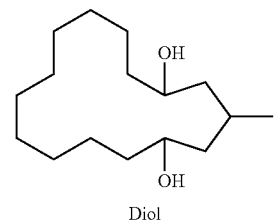

Monool

+

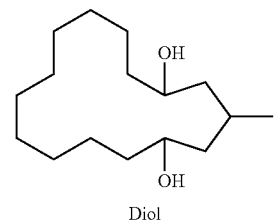

Lactol

+

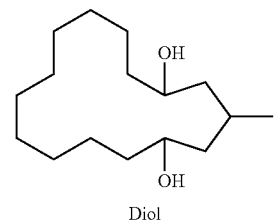

Diol

WO 2017/089327 has reported a method including hydrogenating a diketone to a diol and then partially oxidizing the diol in the presence of Raney copper. This method, however, uses two conversion steps from a diketone. Moreover, the partial oxidization of a diol to an end ether leaves raw material residues and forms excessively oxidized compounds. Therefore, distillation is necessary to obtain an end ether.

[Chemical Formula 3]

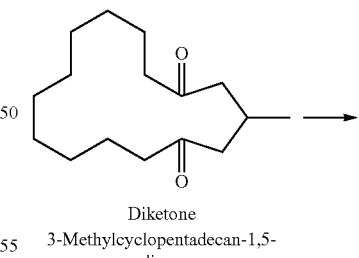

Diketone
3-Methylcyclopentadecan-1,5-dione

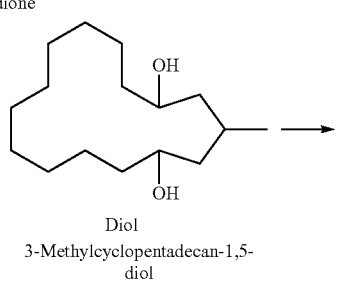

Diol
3-Methylcyclopentadecan-1,5-diol

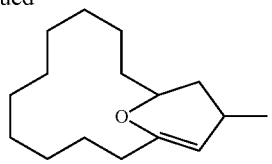

Enol ether
14-Methyl-16-oxabicyclo[10.3.1]hexadec-12-ene

JP 2017-505835 A has reported that 3-methylcyclopentadec-5-ene-1-one and 3-methylcyclopentadec-4-en-1-one can be obtained by treating hydroxy ketone (3R)-5-hydroxy-3-methylcyclopentadecan-1-one or an enol ether (i.e., (14R)-14-methyl-16-oxabicyclo[10.3.1]hexadec-12 ene) with a strong acid. To avoid formation of a diol, the reaction mixture may also contain 3-methylcyclopentadecan-1,5-dione (diol).

JPS56-46881 A has reported that 14-methyl-16-oxabicyclo[10.3.1]hexadec-12-ene (end other) is produced by treating 3-methylcyclopentadecan-1,5-diol (diol) with Raney copper.

[Chemical Formula 4]

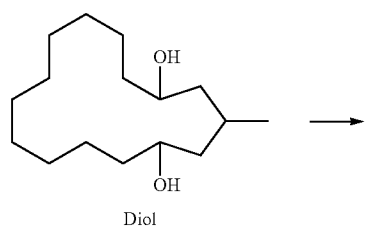

Diol
3-Methylcyclopentadecan-1,5-diol

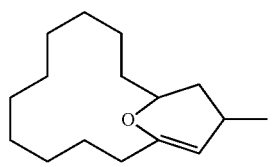

Enol ether
14-Methyl-16-oxabicyclo[10.3.1]hexadeo-12-ene

WO 2018/011386 has reported that a mixture of 3-methylcyclopentadecan-5-ol-1-one and 14-methyl-16-oxabicyclo[10.3.1]hexadec-12-ene (enol ether) is produced by reacting 3-methylcyclopentadecan-1,5-dione (diol) in the presence of sodium borohydride.

DISCLOSURE OF INVENTION

The present invention relates to a method for producing a compound represented by general formula (I), including a step of reacting a compound represented by general formula (II) in the presence of a metal catalyst containing at least one metal element selected from the group consisting of magnesium, aluminum, zirconium, titanium, and samarium, and an alcohol containing at least one selected from the group consisting of a primary alcohol and a secondary alcohol to obtain the compound represented by general formula (I).

[Chemical Formula 5]

 (I)

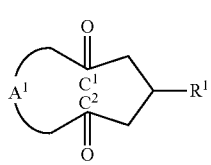 (II)

In the above formulae, the group $-A^1-$ (where the front bond denotes a bond that bonds with a carbon atom $C^1$ while the back bond denotes a bond that bonds with a carbon atom $C^2$) is an alkylene group with 4 or more and 16 or less of carbon atoms that may optionally contain a hetero atom and that may optionally have a substituent, and $R^1$ is hydrogen or an alkyl group with 1 or more and 6 or less of carbon atoms.

The present invention further relates to a method for producing a compound represented by general formula (III), including steps of reacting a compound represented by general formula (II) in the presence of a metal catalyst containing at least one metal element selected from the group consisting of magnesium, aluminum, zirconium, titanium, and samarium, and an alcohol containing at least one selected from the group consisting of a primary alcohol and a secondary alcohol to obtain a compound represented by general formula (I); and decyclizing the resultant compound represented by general formula (I) to obtain the compound represented by general formula (III).

[Chemical Formula 6]

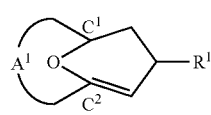 (I)

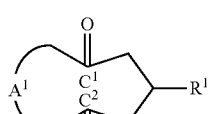 (II)

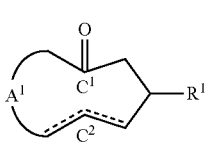 (III)

In the above formulae, the group $-A^1-$ (where the front bond denotes a bond that bonds with a carbon atom $C^1$ while the back bond denotes a bond that bonds with a carbon atom $C^2$) is an alkylene group with 4 or more and 16 or less of carbon atoms that may optionally contain a hetero atom and that may optionally have a substituent, and $R^1$ is hydrogen or an alkylene group with 1 or more and 6 or less of carbon atoms.

The present invention further relates to use of a metal catalyst containing at least one metal element selected from the group consisting of magnesium, aluminum, zirconium, titanium, and samarium, the metal catalyst catalyzing a reaction of a compound represented by general formula (II) into a compound represented by general formula (I) in the presence of an alcohol containing at least one selected from the group consisting of a primary alcohol and a secondary alcohol.

[Chemical Formula 7]

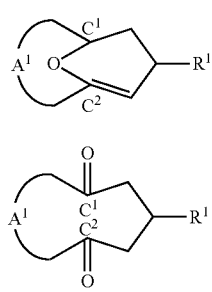

The group -$A^1$- (where the front bond denotes a bond that bonds with a carbon atom $C^1$ while the back bond denotes a bond that bonds with a carbon atom $C^2$) is an alkylene group with 4 or more and 16 or less of carbon atoms that may optionally contain a hetero atom and that may optionally have a substituent, and $R^1$ is hydrogen or an alkyl group with 1 or more and 6 or less of carbon atoms.

DETAILED DESCRIPTION OF THE INVENTION

Only known methods to produce an enol ether using a diketone of a macrocyclic compound as a starting material are a one-step method of performing partial reduction that is difficult to control, and a two-step method including reducing a diketone to a diol and performing partial oxidation in the presence of Raney copper described above.

[Chemical Formula 8]

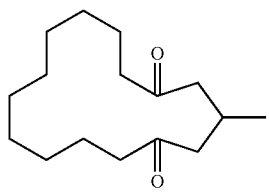

Diketone
3-Methylcyclopentadecan-1,5-dione

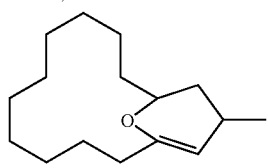

Enol ether
14-Methyl-16-oxabicyclo[10.3.1]
hexadeo-12-ene

An object of the present invention is to provide a method for producing an enol ether in one step using a diketone of a macrocyclic compound as a starting material.

Surprisingly, the present inventors have found that an enol ether can be produced in one step with high selectivity from the diketone in the presence of a specific metal catalyst and a specific alcohol.

Specifically, the present invention relates to a method for producing a compound represented by general formula (I) (hereinafter, also referred to as a "compound of formula (I)" or "compound (I)"), including a step of reacting a compound represented by general formula (II) in the presence of a metal catalyst containing at least one metal element selected from the group consisting of magnesium, aluminum, zirconium, titanium, and samarium, and an alcohol containing at least one selected from the group consisting of a primary alcohol and a secondary alcohol to obtain the compound represented by general formula (I).

[Chemical Formula 9]

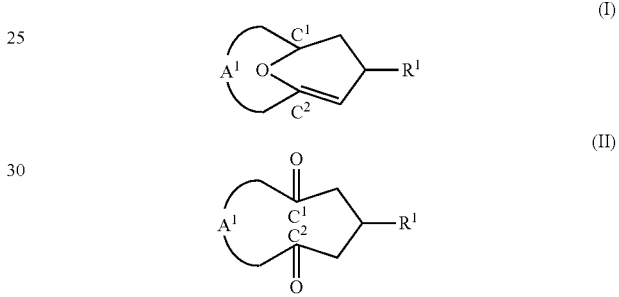

In the above formulae, the group -$A^1$- (where the front bond denotes a bond that bonds with a carbon atom $C^1$ while the back bond denotes a bond that bonds with a carbon atom $C^2$) is an alkylene group with 4 or more and 16 or leas (if carbon atoms that may optionally contain a hetero atom and that may optionally have a substituent, and $R^1$ is hydrogen or an alkyl group with 1 or more and 6 or less of carbon atoms.

The present invention further relates to a method for producing a compound represented by general formula (III), including stops of reacting a compound represented by general formula (II) in the presence of a metal catalyst containing at least one metal dement selected from the group consisting of magnesium, aluminum, zirconium, titanium, and samarium, and an alcohol containing at least one selected from the group consisting of a primary alcohol and a secondary alcohol to obtain a compound represented by general formula (I); and decyclizing the resultant compound represented by general formula (I) to obtain the compound represented by general formula (III).

[Chemical Formula 10]

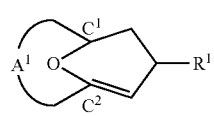

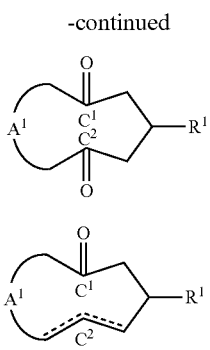

(II)

(III)

In the above formulae, the group -$A^1$- (where the front bond denotes a bond that bonds with a carbon atom $C^1$ while the back bond denotes a bond that bonds with a carbon atom $C^2$) is an alkylene group with 4 or more and 16 or less of carbon atoms that may optionally contain a hetero atom and that may optionally have a substituent, and $R^1$ is hydrogen or an alkyl group with 1 or more and 6 or less of carbon atoms.

Further, the present invention relates to use of a metal catalyst containing at least one metal element selected from the group consisting of magnesium, aluminum, zirconium, titanium, and samarium, the metal catalyst catalyzing a reaction of a compound represented by general formula (II) into a compound represented by general formula (I) in the presence of an alcohol containing at least one selected from the group consisting of a primary alcohol and a secondary alcohol.

[Chemical Formula 11]

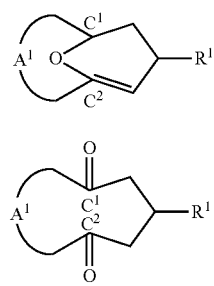

The group -$A^1$- (where the front bond denotes a bond that bonds with a carbon atom $C^1$ while the back bond denotes a bond that bonds with a carbon atom $C^2$) is an alkylene group with 4 or mare and 16 or less of carbon atoms that may optionally contain a hetero atom and that may optionally have a substituent, and $R^1$ is hydrogen or an alkyl group with 1 or more and 6 or less of carbon atoms.

According to the present invention, an enol ether can be produced in one step with high selectivity from the diketone in the presence of a specific metal catalyst and a specific alcohol.

<Compound of Formula (I), Compound of Formula (II), and Compound of Formula (III)>

In the above formulae (I), (II) and (III), "an alkylene group with 4 or more and 16 or less of carbon atoms" in the phrase "an alkylene group with 4 or more and 16 or less of carbon atoms that may optionally contain a hetero atom and that may optionally have a substituent" in the group -$A^1$- is represented by, e.g., a group —$(CH_2)_4$—, a group —$(CH_2)_5$—, a group —$(CH_2)_6$—, a group —$(CH_2)_7$—, a group —$(CH_2)_8$—, a group —$(CH_2)_9$—, a group —$(CH_2)_{10}$—, a group —$(CH_2)_{11}$—, a group —$(CH_2)_{12}$—, a group —$(CH_2)_{13}$—, a group —$(CH_2)_{14}$— a group —$(CH_2)_{15}$—, or a group —$(CH_2)_{16}$—. From the viewpoint of using the resultant compound of general formula (I) as a precursor of a perfume compound, "an alkylene group with 4 or more and 16 or less of carbon atoms" is preferably a group —$(CH_2)_4$—, a group —$(CH_2)_6$—, a group —$(CH_2)_8$—, a group —$(CH_2)_{10}$—, a group —$(CH_2)_{12}$—, a group —$(CH_2)_{14}$—, or a group —$(CH_2)_{16}$—, and more preferably a group —$(CH_2)_6$—, a group a —$(CH_2)_8$—, a group —$(CH_2)_{10}$—, or a group —$(CH_2)_{12}$—.

In the above formulae (I), (II) and (III), "an alkylene group with 4 or more and 16 or less of carbon atoms that may optionally contain a hetero atom" in the phrase "an alkylene group with 4 or more and 16 or less of carbon atoms that may optionally contain a hetero atom and that may optionally have a substituent" in the group -$A^1$- may contain, as a hetero atom, oxygen, nitrogen, and/or a sulfur atom. Specifically, "an alkylene group with 4 or more and 16 or less of carbon atoms that may optionally contain a hetero atom" is an alkylene group with 4 or more and 16 or less of carbon atoms that may contain an ether bond (—O—), an ester bond (—C(=O)—O— or —O—C(=O)—), a secondary amino group (—NH—), a thioether group (—S—), or a combination thereof that does not inhibit reaction. Examples of the "alkylene group with 4 or more and 16 or less of carbon atoms that may contain an ether bond, an ester bond, a secondary amino group, a thioether group, or a combination thereof" include a group —$(CH_2)_2$—O—$(CH_2)_2$—, a group —$(CH_2)_2$—O—$(CH_2)_6$—, a group —$(CH_2)_3$—O—$(CH_2)_5$—, a group —$(CH_2)_4$—O—$(CH_2)_4$—, a group —$(CH_2)_2$—O—$(CH_2)_7$—, a group —$(CH_2)_3$—O—$(CH_2)_6$—, a group —$(CH_2)_4$—O—$(CH_2)_6$—, a group —$(CH_2)$—O—$(CH_2)_9$—, a group —$(CH_2)_2$—O—$(CH_2)_2$—O—$(CH_2)_8$—, a group —$(CH_2)_3$—O—$(CH_2)_7$—, a group —$(CH_2)_4$—O—$(CH_2)_6$—, a group —$(CH_2)_5$—O—$(CH_2)_5$—, and a group —$(CH_2)_2$—NH—$(CH_2)_2$—. From the viewpoint of using the resultant compound of general formula (I) as a precursor of a perfume compound, a group —$(CH_2)$—O—$(CH_2)_3$—, a group —$(CH_2)_2$—O—$(CH_2)_8$—, a group —$(CH_2)_3$—O—$(CH_2)_7$—, a group —$(CH_2)_4$—O—$(CH_2)_6$—, and a group —$(CH_2)_5$—O—$(CH_2)_5$— are preferred.

Further, "an alkylene group with 4 or more and 16 or loss of carbon atoms that may optionally have a substituent" in the phrase "an alkylene group with 4 or more and 16 or less of carbon atoms that may optionally contain a hetero atom and that may optionally have a substituent" in the group -$A^1$- is an alkylene group with 4 or more and 16 or less of carbon atoms that may have at least one substituent, preferably have one or two substituents. Examples of the substituent include an alkyl group, an alkoxy group, an alkylamino group, an alkoxycarbonyl group, an alkanoyl group, an aryl group, an aralkyl group, an aryloxy group, an acyloxy group, a carboxy group, a halogen, atom, a carbon ring and a heterocyclic ring, and it is preferably an alkyl group, an alkoxycarbonyl group, or an alkoxy group, and more preferably an alkyl group.

Two fir more of the substituents may be bonded to each other to form a carbon ring or a heterocyclic ring.

In the above formulae (I), (II) and (III), $R^1$ is hydrogen or an alkyl group with 1 or more and 6 or less of carbon atoms. From the viewpoint of using the resultant compound of general formula (I) as a precursor of a perfume compound, $R^1$ is preferably a hydrogen atom or an alkyl group with 1 or more and 3 or less of carbon atoms, more preferably a hydrogen atom, —CH$_3$, or —C$_2$H$_5$, and further preferably —CH$_3$.

The compound represented by general formula (II) is represented, for example, by the following formulae. From the viewpoint of using the resultant compound of general formula (I) as a precursor of a perfume compound, it is preferably a compound represented by formula (vi), a compound represented by formula (vii), a compound represented by formula (viii), a compound represented by formula (ix), or a compound represented by formula (x), and more preferably a compound represented by formula (vii) or a compound represented by formula (viii). The compound represented by formula (vii) is 3-methylcyclopentadecan-1,5-dione.

[Chemical Formula 12]

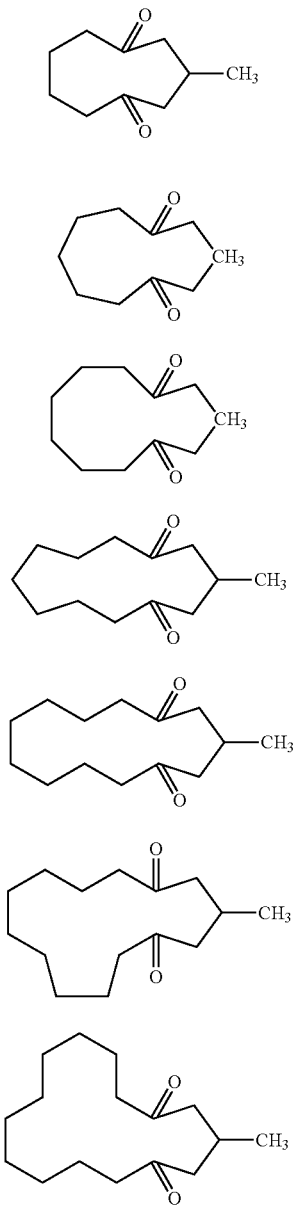

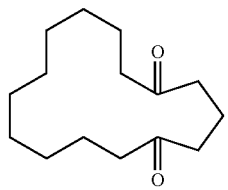

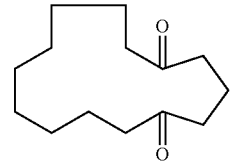

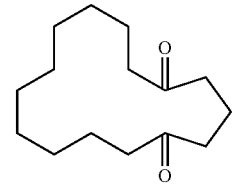

The compound represented by general formula (I) is, e.g., 14-methyl-16-oxabicyclo[10.3.1]hexadecan-12-ene represented by formula (7) below.

[Chemical Formula 13]

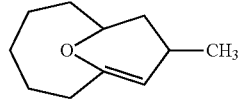

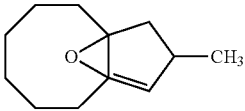

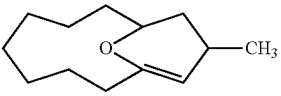

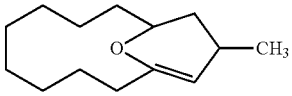

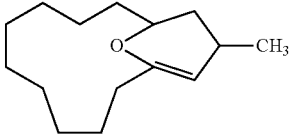

(7)

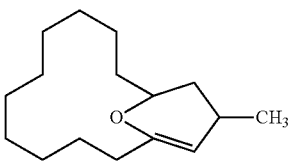

The compound represented by general formula (III) is, e.g., muscenone represented by formula (18) below.

[Chemical Formula 14]

(11)

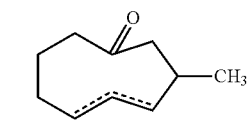

(12)

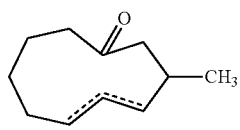

(13)

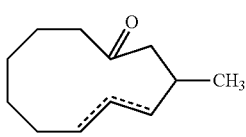

(14)

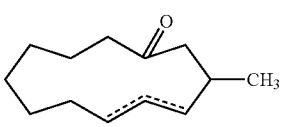

(15)

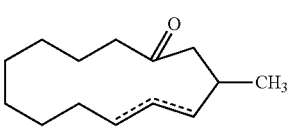

(16)

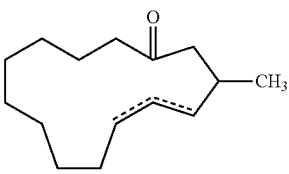

(18)

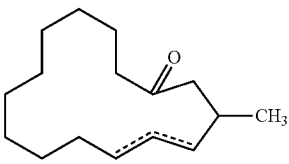

(19)

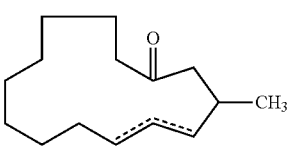

(20)

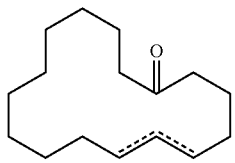

The compound represented by general formula (II) can be obtained by a known method, e.g., the method described in JP 2016-124867 A.

<Metal Catalyst>

In the present invention, the metal catalyst is a metal catalyst containing at least one metal element selected from the group consisting of magnesium, aluminum, zirconium, titanium, and samarium. Preferably, the metal catalyst contains at least one metal element selected from the group consisting of aluminum, zirconium, and titanium. The metal catalyst may be, e.g., aluminum alkoxide, zirconium alkoxide, titanium alkoxide, or zirconium oxide. Examples of the aluminum alkoxide include aluminum ethoxide, aluminum isopropoxide, aluminum n-butoxide, aluminum sec-butoxide, and aluminum tert-butoxide. The catalyst containing zirconium may be, e.g., zirconia (zirconium dioxide) or zirconium alkoxide. Examples of the zirconium alkoxide include zirconium (IV) ethoxide, zirconium (IV) isopropoxide, zirconium (IV) n-propoxide, zirconium (IV) n-butoxide, zirconium (IV) sec-butoxide, and zirconium (IV) tert butoxide. The metal catalyst is preferably aluminum alkoxide, zirconium alkoxide, or titanium alkoxide, and menu preferably aluminum alkoxide or zirconium alkoxide because of their high catalytic activity (i.e., high reaction rate and high reaction yield). The metal catalyst is preferably zirconium alkoxide, and more preferably zirconium(IV) n-butoxide, zirconium sec-butoxide, or zirconium tert-butoxide, because the amount of use can be reduced to a catalytic amount. The metal catalyst is preferably zirconium (IV) n-butoxide because it is industrially easily available.

<Alcohol>

In the present invention, the alcohol is an alcohol containing at least one selected from the group consisting of a primary alcohol and a secondary alcohol. Examples of the primary alcohol include ethanol, 1-propanol, 1-butanol, 2-methylpropanol, 1-pentanol, 2-methylbutanol, 3-methylbutanol, 1-hexanol, 2-methylpentanol, 3-methylpentanol, 2-ethylbutanol, 1-heptanol, 2-methylhexanol, 1-octanol, 1-nonanol, and 1-decanal. As the secondary alcohol, the valence is not limited and any secondary alcohol that has at least one secondary hydroxyl group may be used. The secondary alcohol may have a linear, branched, or cyclic aliphatic group or aromatic group, or both of them. Examples of the secondary alcohol include isopropyl alcohol, 2-butanol, 2-pentanol, 3-pentanol, cyclopentanol, 2-hexanol, 3-hexanol, cyclohexanol, 3-methyl-2-pentanol, 4-methyl-2-pentanol, 2-heptanol, 3-heptanol, 4-heptanol, 3-methyl-2-hexanol, 4-methyl-2-hexanol, 5-methyl-2-hexanol, cycloheptanol, 2-octanol, 3-octanol, 4-octanol, cyclooctanol, 2-nonanol, 3-nonanol, 4-nonanol, and 5-nonanol. As the secondary alcohol, cyclohexanol and 2-octanol are preferred because they can accelerate the reaction rate with temperature rise.

The alcohol is preferably a secondary alcohol. The alcohol is preferably an alcohol having a boiling point of 100° C. or higher because it can improve the reaction selectivity and shorten the reaction time by causing the reaction to proceed while removing water as a by-product out of the system. Meanwhile, the alcohol is preferably an alcohol having a boiling point of 200° C. or lower because the boiling point is adequate and reaction does not proceed excessively during azeotrope with water so that a decrease in the reaction selectivity can be avoided. The alcohol is preferably an alcohol having a boiling point of 150° C. or higher and 200° C. or lower because it can accelerate the reaction rate with temperature rise. Specifically, isopropanol has a bailing point of 82.4° C., cyclohexanol has a bailing point of 161.8° C., 2-butanol has a boiling point of 100° C., and 2-octanol has a boiling point of 174° C. The alcohol containing at least one selected from the group consisting of a primary alcohol and a secondary alcohol is preferably 2-octanol or cyclohexanol because they are industrially easily available.

<Reaction Temperature>

In the present invention, the step of reacting the compound of formula (II) in the presence of the metal catalyst and the alcohol to obtain the compound of formula (I) is carried out, e.g., at 80° C. or higher, preferably at 100° C. or higher, more preferably at 150° C. or higher; and, e.g., at 280° C. or lower, preferably at 250° C. or fewer, and more preferably at 190° C. or fewer.

<Reaction Time>

In the present invention, the reaction time for the step of reacting the compound of formula (II) in the presence of the metal catalyst and the alcohol to obtain the compound of formula (I) is, e.g., two hours to five days, preferably four hours to two days, and from the viewpoints of the production cost and the production efficiency, more preferably six hours to 24 hours.

<Charge>

In the present invention, in the step of reacting the compound of formula (II) in the presence of the metal catalyst and the alcohol to obtain the compound of formula (I), the mole ratio of the compound of formula (II) to the alcohol (compound of formula (II): alcohol) is, e.g., 1:1 to 1:100, preferably 1:1 to 1:50, and from the viewpoints of the production cost and the production efficiency, more preferably 1:1.5 to 1:5.

In one specific embodiment, the metal catalyst, the alcohol, and the compound represented by general formula (II) are mixed in a reactor, and the reaction is carried out at a predetermined temperature generally while stirring. The metal catalyst, the alcohol, and the compound represented by general formula (II) may be added in any order, and an additive may be added further as needed. More preferably, a Dean-Stark apparatus or a rectification column is attached to the reactor to carry out the reaction. After completion of the reaction, the compound represented by general formula (I) may be purified by distillation.

In the present invention, in the step of reacting the compound of formula (II) in the presence of the metal catalyst and the alcohol to obtain the compound of formula (I), when the metal catalyst is a metal catalyst containing zirconium, the mole ratio of the compound of formula (II) to the metal catalyst (compound of formula (II): metal catalyst) is, e.g., 1:0.001 to 1:1.5, preferably 1:0.01 to 1:1.2, and from the viewpoint of the production coat, more preferably 1:0.05 to 1:1.1. Moreover, when the metal catalyst is a metal catalyst containing at least one metal element selected from the group consisting of magnesium, aluminum, titanium, and samarium, the mole ratio of the compound of formula (II) to the metal catalyst (compound of formula (II): metal catalyst) is, e.g., 1:0.3 to 1:3, preferably 1:0.5 to 1:1.5, and from the viewpoint of the production cost, more preferably 1:0.8 to 1:1.2.

<Additive>

In the present invention, the step of reacting the compound of formula (II) in the presence of the metal catalyst and the alcohol to obtain the compound of formula (I) may be carried out in the presence of an additive. The additive may be, e.g., acid, diol, diamine, or amino alcohol. Examples of the acid include phosphoric acid, sulfuric acid, paratoluenesulfonic acid, acetic acid, chloroacetic acid, and trifluoroacetic acid (TFA). Examples of the diol include ethylene glycol (EG), 1,2-cyclohexanediol, 1,3-propanediol, 1,4-butanediol, 1,5-pentanediol, and 1,6-hexanediol Examples of the diamine include ethylenediamine, 1,2-diaminocyclohexane, and 1,2-phenylenediamine. Examples of the amino alcohol include 2-aminoethanol, 3-aminopropanol, 2-aminopropanol, 1-amino-2-propanol, valinol, and phenylalaninol. As the additive, acid and diol are preferred, and TEA and EG are more preferred from the viewpoint of shortening the reaction time. In the case of using the acid as the additive, the mole ratio of the metal catalyst to the acid (metal catalyst:acid) is, e.g., 1:0.05 to 1:5, preferably 1:1 to 1:3. In the case of using the diol as the additive, the mote ratio of the metal catalyst to the diol (metal catalyst:diol) is, e.g., 1:0.1 to 1:5, preferably 1:1 to 1:8. In the case of using the acid and the diol as the additive, the mole ratio of the metal catalyst to the acid and the diol (metal catalyst:acid: diol) is, e.g., 1:0.1 to 5:0.1 to 5, preferably 1:1 to 3:1 to 3.

The present invention further relates to a method for producing a compound represented by general formula (III), including steps of reacting a compound represented by general formula (II) in the presence of a metal catalyst containing at least one metal element selected from the group consisting of magnesium, aluminum, zirconium, titanium, and samarium, and an alcohol containing at least one selected from the group consisting of a primary alcohol and a secondary alcohol to obtain a compound represented by general formula (I); and decyclizing the resultant compound represented by general formula (I) to obtain the compound represented by general formula (III).

[Chemical Formula 15]

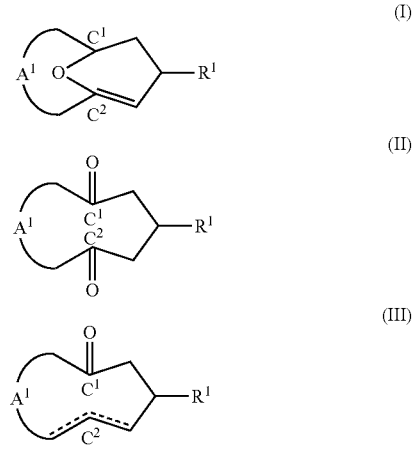

In the above formulae, the group -$A^1$- (where the front bond denotes a bond that bonds with a carbon atom $C^1$ while the hack bond denotes a bond that bonds with a carbon atom $C^2$) is an alkylene group with 4 or more and 16 or less of carbon atoms that may optionally contain a hetero atom and that may optionally have a substituent, and $R^1$ is hydrogen or an alkyl group with 1 or more and 6 or leas of carbon atoms.

<Step of Reacting the Compound of Formula (II) in the Presence of the Metal Catalyst and the Alcohol to Obtain the Compound of Formula (I)>

The step can be carried out in the same manner as the step in the production method of the compound represented by general formula (I).

<Step of Decyclizing the Compound of Formula (I) to Obtain the Compound of Formula (III)>

An exemplary method for decyclizing the compound of formula (I) is a decyclization method carried out in the presence of an acid. The acid may be, e.g., sulfuric acid, phosphoric acid, or benzenesulfonic acid. Phosphoric acid is preferred from the viewpoints of handleability and the reaction yield. The amount of the acid in terms of the mole ratio of the compound of formula (I) to the acid (compound of formula (I): acid) is preferably 1:0.01 to 1:1, and more preferably 1:0.1 to 1:0.5 from the viewpoints of the production efficiency and the reaction yield.

The reaction temperature in the decyclization reaction step is preferably at 20° C. or higher, more preferably at 50° C. or higher, and further preferably at 70° C. or higher from the viewpoint of improving the reaction yield, while it is preferably at 200° C. or lower, more preferably at 150° C. or lower, and further preferably at 130° C. or lower from the viewpoint of reducing side reactions.

The reaction time in the decyclization reaction step is preferably 0.5 hour or more, and more preferably one hour or more, while it is preferably 20 hours or less, more preferably ten hours or less, and further preferably than five hours or less from the viewpoint of improving the reaction yield.

The decyclization reaction step may be carried out in the presence of an organic solvent. The organic advent is nut particularly limited as long as it forms an azeotrope with water. Examples of the organic solvent include hydrocarbons, and toluene is preferred from the viewpoint of dehydration efficiency.

Further, the present invention relates to use of a metal catalyst containing at least one metal element selected from the group consisting of magnesium, aluminum, zirconium, titanium, and samarium, the metal catalyst catalyzing a reaction of a compound represented by general formula (II) into a compound represented by general formula (I) in the presence of an alcohol containing at least one selected from the group consisting of a primary alcohol and a secondary alcohol.

[Chemical Formula 16]

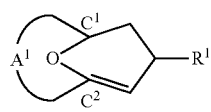
(I)

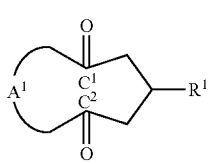
(II)

The group -$A^1$- (where the front bond denotes a bond that bonds with a carbon atom $C^1$ while the back bond denotes a bond that bonds with a carbon atom $C^2$) is an alkylene group with 4 or more and 16 or leas of carbon atoms that may optionally contain a hetero atom and that may optionally have a substituent, and $R^1$ is hydrogen or an alkyl group with 1 or more and 6 or less of carbon atoms.

In use of the metal catalyst, the metal catalyst, the compound represented by general formula (II), the compound represented by general formula (I), and the alcohol are as described above.

In use of the metal catalyst, the metal catalyst catalyzes a reaction of the compound represented by general formula (II) into the compound represented by general formula (I) in the presence of the alcohol containing at least one selected from the group consisting of the primary alcohol and the secondary alcohol. The amount of the metal catalyst is adjusted so that when the metal catalyst is a metal catalyst containing zirconium, the mole ratio of the compound of formula (I) to the metal catalyst (compound of formula (II): metal catalyst) is e.g., 1:0.001 to 1:1.5, preferably 1:0.01 to 1:1.2, and from the viewpoint of the production cost, more preferably 1:0.05 to 1:1.1. Further, the amount of the metal catalyst is adjusted so that when the metal catalyst is a metal catalyst containing at least one metal element selected from the group consisting of magnesium, aluminum, titanium, and samarium, the mole ratio of the compound of formula (II) to the metal catalyst (compound of formula (II): metal catalyst) is, e.g., 1:0.3 to 1:3, preferably 1:0.5 to 1:1.5, and from the viewpoint of the production cost, more preferably 1:0.8 to 1:1.2.

With regard to the embodiments described above, the present invention further discloses production methods of the compound represented by general formula (I).

<1> A method for producing a compound represented by general formula (I), including a step of reacting a compound represented by general formula (II) in the presence of a metal catalyst containing at least one metal element selected from the group consisting of magnesium, aluminum, zirconium, titanium, and samarium, and an alcohol containing at least one selected from the group consisting of a primary alcohol and a secondary alcohol to obtain the compound represented by general formula (I).

[Chemical Formula 17]

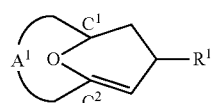
(I)

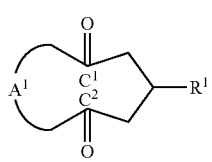
(II)

In the above formulae, the group -$A^1$- (where the front bond denotes a bond that bonds with a carbon atom $C^1$ while the back bond denotes a bond that bonds with a carbon atom $C^2$) is an alkylene group with 4 or more and 16 or less of carbon atoms that may optionally contain a hetero atom and that may optionally have a substituent, and $R^1$ is hydrogen or an alkyl group with 1 or more and 6 or leas of carbon atoms.

<2> The method according to <1>, wherein the metal element of the metal catalyst is preferably at least one selected from the group consisting of aluminum, zirconium, and titanium, and preferably zirconium.

<3> The method according to <1> or <2>, wherein the metal catalyst is preferably at least one selected from the group consisting of aluminum alkoxide, zirconium alkoxide, and titanium alkoxide, more preferably at least one selected from aluminum alkoxide and zirconium alkoxide, and further preferably zirconium alkoxide.

<4> The method according to any one of <1> to <4>, wherein the group -$A^1$- is an alkylene group with 4 or more and 16 or less of carbon atoms that may optionally contain a hetero atom and that may optionally have a substituent, preferably an alkylene group with 4 or more and 16 or less of carbon atoms that may optionally contain a hetero atom, further preferably an alkylene group with 6 or more and 14 or less of carbon atoms that may optionally contain a hetero atom, and still further preferably an alkylene group with 8 or more and 12 or less of carbon atoms that may optionally contain a hetero atom.

<5> The method according to any one of <1> to <4>, wherein $R^1$ is preferably hydrogen or an alkyl group with 1 or more and 6 or less of carbon atoms, more preferably hydrogen or a saturated alkyl group with 1 or more and 3 or less of carbon atoms, further preferably —H, —$CH_3$, or —$C_2H_5$, and still further preferably —$CH_3$.

<6> The method according to any one of claims 1 to 5, wherein the alcohol preferably contains a secondary alcohol, more preferably contains isopropanol, cyclohexanol, 2-butanol, or 2-octanol, and further preferably contains cyclohexanol or 2-octanol.

<7> The method according to any one of <1> to <6>, wherein the reaction temperature is 100° C. or higher and 250° C. or lower.

<8> The method according to any one of <1> to <7>, wherein the mole ratio of the compound of formula (II) to the alcohol (compound of formula (II): alcohol) is preferably 1:1 to 1:100, more preferably 1:1 to 1:50, more preferably 1:1 to 1:10, more preferably 1:1 to 1:5, and more preferably 1:1.5 to 1:5.

<9> The method according to any one of <1> to <8>, wherein the mole ratio of the compound of formula (II) to the metal catalyst (compound of formula (II): metal catalyst) is 1:0.01 to 1:1.2 when the metal catalyst is a metal catalyst containing zirconium.

<10> The method according to any one of <1> to <8>, wherein the mole ratio of the compound of formula (II) to the metal catalyst (compound of formula (II): metal catalyst) is 1:0.5 to 1:1.5 when the metal catalyst is a metal catalyst containing at least one metal element selected from the group consisting of magnesium, aluminum, titanium, and samarium.

<11> The method according to <1>, wherein the metal element of the metal catalyst is at least one selected from the group consisting of aluminum, zirconium, and titanium, the group -$A^1$- is an alkylene group with 4 or more and 16 or less of carbon atoms that may optionally contain a hetero atom, $R^1$ is —H, —$CH_3$, or —$C_2H_5$, and the alcohol contains a secondary alcohol.

<12> The method according to <1>, wherein the metal element of the metal catalyst is aluminum or zirconium, the group -$A^1$- is an alkylene group with 4 or more and 16 or less of carbon atoms that may optionally contain a hetero atom, $R^1$ is —H, —$CH_2$ or —$C_2H_5$, and the alcohol contains isopropanol cyclohexanol 2-butanol or 2-octanol.

<12> The method according to <1>, wherein the group -$A^1$- is an alkylene group with 4 or more and 16 or less of carbon atoms, $R^1$ is —H, —$CH_3$, or —$C_4H_5$, the alcohol contains a secondary alcohol, and the mole ratio of the compound of formula (II) to the alcohol (compound of formula (II): alcohol) is 1:1 to 1:50.

<13> The method according to <1>, wherein the group -$A^1$- is an alkylene group with 6 or more and 14 or less of carbon atoms, $R^1$ is —H, —$CH_3$, or —$C_2H_5$, the alcohol contains a secondary alcohol, and the mole ratio of the compound of formula (II) to the alcohol (compound of formula (II): alcohol) is 1:1 to 1:10.

<14> The method according to <1>, wherein the metal element of the metal catalyst is zirconium, the group -$A^1$- is an alkylene group with 4 or more and 16 or less of carbon atoms that may optionally contain a hetero atom, $R^1$ is —H, —$CH_3$ or —$C_2H_5$, and the mole ratio of the compound of formula (II) to the metal catalyst (compound of formula (II): metal catalyst) is 1:0.01 to 1:1.2.

<15> The method according to <1>, wherein the metal element of the metal catalyst is zirconium, the group -$A^1$- is an alkylene group with 4 or more and 16 or less of carbon atoms that may optionally contain a hetero atom, $R^1$ is —H, —$CH_3$, or —$C_2H_5$, the alcohol contains isopropanol cyclohexanol, 2-butanol or 2-octanol and the mole ratio of the compound of formula (II) to the metal catalyst (compound of formula (II): metal catalyst) is 1:0.01 to 1:1.2.

<16> The method according to <1>, wherein the metal element of the metal catalyst is at least one selected from the group consisting of magnesium, aluminum, titanium, and samarium, the group -$A^1$- is an alkylene group with 4 or more and 16 or less of carbon atoms that may optionally contain a hetero atom, $R^1$ is —H, —$CH_3$, or —$C_2H_5$, and the mole ratio of the compound of formula (I) to the metal catalyst (compound of formula (II): metal catalyst) is 1:0.5 to 1:1.5.

<17> The method according to <1>, wherein the metal element of the metal catalyst is at least one selected from the group consisting of magnesium, aluminum, titanium, and samarium, the group -$A^1$- is an alkylene group with 4 or more and 16 or less of carbon atoms that may optionally contain a hetero atom, $R^1$ is —H, —$CH_3$, or —$C_2H_5$ the alcohol contains isopropanol, cyclohexanol, 2-butanol, or 2-octanol, and the mole ratio of the compound of formula (ED to the metal catalyst (compound of formula (II): metal catalyst) is 1:0.5 to 1:1.5.

<18> A method for producing a compound represented by general formula (III), including a step of decyclizing the compound represented by general formula (I) obtained in the method according to <1> to <17> to obtain the compound represented by general formula (III).

<19> A method for producing a compound represented by general formula (III), including steps of reacting a compound represented by general formula (II) in the presence of a metal catalyst containing at least one metal element selected from the group consisting of magnesium, aluminum, zirconium, titanium, and samarium, and an alcohol containing at least one selected from the group consisting of a primary alcohol and a secondary alcohol to obtain a compound represented by general formula (I): and decyclizing the resultant compound represented by general formula (I) to obtain the compound represented by general formula (III).

[Chemical Formula 18]

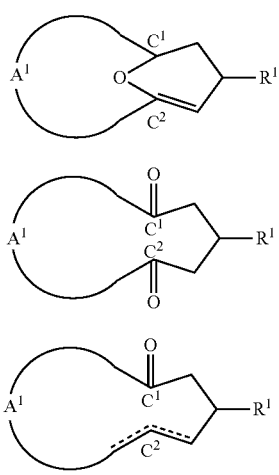

In the above formulae, the group -A$^1$- (where the front bond denotes a bond that bonds with a carbon atom C$^1$ while the back bond denotes a bund that bonds with a carbon atom C$^2$) is an alkylene group with 4 or more and 16 or less of carbon atoms that may optionally contain a hetero atom and that may optionally have a substituent, and R$^1$ is hydrogen or an alkylene group with 1 or more and 6 or loss of carbon atoms.

<20> Use of a metal catalyst containing at least one metal element selected from the group consisting of magnesium, aluminum, zirconium, titanium, and samarium, the metal catalyst catalyzing a reaction of a compound represented by general formula (II) into a compound represented by general formula (I) in the presence of an alcohol containing at least one selected from the group consisting of a primary alcohol and a secondary alcohol.

[Chemical Formula 19]

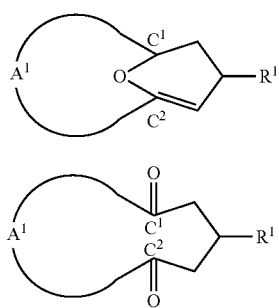

The group -A$^1$- (where the front bond denotes a bond that bonds with a carbon atom C$^1$ while the back bond denotes a bond that bonds with a carbon atom C$^2$) is an alkylene group with 4 or more and 16 or less of carbon atoms that may optionally contain a hetero atom and that may optionally have a substituent, and R$^1$ is hydrogen or an alkyl group with 1 or more and 6 or less of carbon atoms.

<21> The use according to <20>, wherein the amount of the metal catalyst is adjusted so that when the metal catalyst is a metal catalyst containing zirconium, the mole ratio of the compound of formula (II) to the metal catalyst (compound of formula (II): metal catalyst) is, e.g., 1:0.001 to 1:1.5, preferably 1:0.01 to 1:1.2, and from the viewpoint of the production cost, more preferably 1:0.05 to 1:1.1, and when the metal catalyst is a metal catalyst containing at least one metal element selected from the group consisting of magnesium, aluminum, titanium, and samarium, the mole ratio of the compound of formula (II) to the metal catalyst (compound of formula (II): metal catalyst) is, e.g., 1:0.3 to 1:3, preferably 1:0.5 to 1:1.5, and from the viewpoint of the production cost, more preferably 1:0.8 to 1:1.5.

<Apparatus and Analytical Conditions for Gas Chromatography>

GC Apparatus: Manufactured by Agilent Technologies, Inc., Type: GC-6850

Column: Manufactured by J&W, DB-1 (inner diameter: 0.25 mm, length: 30 m, and film thickness: 0.25 μm)

Carrier Gas: He, 1.5 mL/min

Injection Condition: 300° C., split ratio: 100/1

Injection Amount: 1 μL

Detection Condition: FID System, 300° C.

Column Temperature Condition: 80° C.→raising the temperature at 10° C./min→300° C. maintained for 10 minutes

[Identification of Compound]

Compounds obtained in the following examples and experimental examples were confirmed to be identical to separately produced compounds using GC (gas chromatography). The separately produced compounds were prepared according to the method described in JPS56-46881 A

[Raw Material Conversion Rate]

The raw material conversion rates in Examples 1-9 were calculated according to the following formula. Note here that the raw material is 3-methylcyclopentadeca-1,5-dione (II-1).

Raw material conversion rate=(Purity of raw material at the start of reaction [GC area %]−Purity of raw material at the end of reaction [GC area %])÷(Purity of raw material at the start of reaction [GC area %])×100

[Reaction Selectivity]

The raw material selectivities in Examples 1-9 were calculated according to the following formula. Note here that the raw material is 3-methylcyclopentadeca-1,5-dione (II-1), and end ether is 14-methyl-16-oxabicyclo[10.3.1]hexadec-12-ene (I-1).

Reaction selectivity=(Purity of enol ether [GC area %])÷(100−Purity of raw material [GC area %])×100

[Raw Material Conversion Rate]

The raw material conversion rates in Examples 10-11 were calculated according to the following formula. Note here that diketone is 3-methylcyclopentadeca-1,5-dione (II-1).

Raw material conversion rate=(Amount of diketone charged [mol]−Amount of diketone obtained after distillation [mol])÷(Amount of diketone charged [mol])×100

*(Amount of diketone obtained after distillation [mol])=(Distillate weight [g])×(Purity [GC area %])÷Molecular weight [g/mol]

[Reaction Selectivity]

The raw material selectivities in Examples 10-11 were calculated according to the following formula. Note that dike tone is 3-methylcyclopentadeca-1,5-dione (II-1), and enol ether obtained is 14-methyl-16-oxabicyclo[10.3.1]hexadec-12-ene (I-1).

Reaction selectivity=(Amount of end ether obtained after distillation [mol])÷(Amount of converted diketone [mol])×100

*(Amount of enol ether obtained after distillation [mol])=(Distillate weight [g])×(Purity [GC area %])÷Molecular weight [g/mol]

Production Example 1

Synthesis of 3-methylcyclopentadecan-1,5-dione (II-1)

In a 1 L four necked flask to which a mechanical stirrer, a thermometer, a septum, and a nitrogen line were attached, orthotungstic acid (5.20 g, 20.8 mmol, 0.05 eq.) and a 60 mass % hydrogen peroxide solution (59.0 g, 1.04 mol, 2.50 eq.) were placed, and the reaction mixture was stirred at room temperature for 20 minutes. Then, t-butyl alcohol (350 g) and 14-methylbicyclo[10.3.0]pentadecene (100 g, 41.6 mmol) were added to the mixture, and the reaction was carried out at 40° C. for 24 hours. After completion of the reaction, a 10 mass % sodium sulfite aqueous solution (150 ml) was added to the reaction mixture under ice cooling for quenching, to which water (100 ml) and hexane (100 ml) were added for layer separation. An aqueous layer was extracted with hexane (100 ml), and a combined organic layer was washed twice with a 10 mass % potassium hydroxide aqueous solution (50 ml). Then, the solvent of the organic layer was evaporated under reduced pressure to obtain 99.0 g of a crude product mainly composed of 3-methylcyclopentadecan-1,5-dione (II-1). The mass of the compound contained in the crude product was measured by gas chromatography internal standard quantitative analysis. As a result, the purity of 3-methylcyclopentadecan-1,5-dione (II-1) was 51.8%.

Example 1

In a 30 ml two-necked flask, 3-methylcyclopentadecan-1,5-dione (II-1) (252 mg, purity: 100%, 1 mmol), aluminum isopropoxide (306 mg, 1.05 mmol, 1.05 eq.), and isopropanol (1.5 ml) were placed. A Dimroth condenser and a septum cap were attached to the flask. Nitrogen blowing was performed at the upper part of the Dimroth condenser. The flask was heated to 110° C. in an oil bath, and the reaction was carried out under heating and reflux for eight hours to obtain a reaction mixture containing 14-methyl-16-oxabicyclo[10.3.1]hexadec-12-ene (I-1). The disappearance of the raw material was confirmed by the GC measurement of the reaction mixture, and then the reaction mixture was coded to the room temperature. As a resulted the GC analysis, the raw material conversion rate was 100%, and the reaction selectivity was 20%.

[Chemical Formula 20]

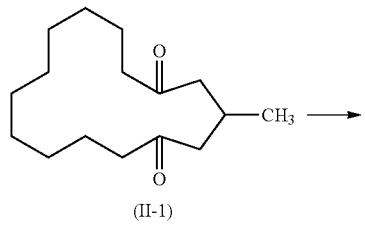

(II-1)

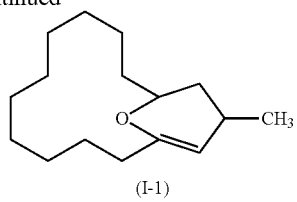

(I-1)

Example 2

In a 30 ml two-necked flask, aluminum isopropoxide (428 mg, 2.10 mmol, 1.05 eq.), trifluoroacetic acid (46 ml, 0.60 mmol, 0.30 eq.), and isopropanol (1.5 ml) were placed. A Dimroth condenser and a septum cap were attached to the flask. Nitrogen blowing was performed at the upper part of the Dimroth condenser. After stirring the reaction mixture at room temperature for one hour, 3-methylcyclopentadecan-1,5-dione (II-1) (504 mg, purity: 100%, 2.00 mmol) was added thereto. The flask was heated to 110° C. in an oil bath, and the reaction was carried out under heating and reflux to obtain a reaction mixture containing 14-methyl-16-oxabicyclo[10.3.1]hexadec-12-ene (I-1). The disappearance of the raw material was confirmed by the GC measurement, and then the reaction mixture was cooled to the room temperature. As a result of the GC analysis of the reaction mixture, the raw material conversion rate was 100%, and the reaction selectivity was 83%.

Example 3

In a 30 ml two-necked flask to which a Dimroth with a nitrogen line and a septum were attached, 3-methylcyclopentadecan-1,5-dione (II-1) (1.0 g, purity-100%, 3.96 mmol), zirconium oxide (ZRO-5) (manufactured by DAIICHI KIGENSO KAGAKU KOGYO CO., LTD., 500 mg, 4.1 mmol, 1.02 eq.), trifluoroacetic acid (0.045 g, 0.40 mmol, 0.10 eq.), and isopropanol (5 g) were placed. Then, the flask was heated to 110° C. in an oil bath, and the reaction was carried out under heating and reflux for 120 hours to obtain a reaction mixture containing 14-methyl-16-oxabicyclo[10.3.1]hexadec-12-ene (I-1). As a result of the GC analysis of the reaction mixture, the raw material conversion rate was 31%, and the reaction selectivity was 24%.

Example 4

The same procedure as in Example 3 was carried out except that isopropanol was changed to cyclohexanol, the temperature was changed from 110° C. to 180° C., and the reaction time was changed from 120 hours to 72 hours. As a result of the GC analysis of the reaction mixture, the raw material conversion rate was 92%, and the reaction selectivity was 72%.

Example 5

In a 30 ml two-necked flask to which a septum and a Dean-Stark tube with a Dimroth were attached, 85% zirconium n-butoxide (536 mg, 1.19 mmol, 0.10 eq.), trifluoroacetic acid (136 mg, 1.19 mmol, 0.10 eq.), and isopropanol (10 ml) were placed. After stirring the mixture in the flask at room temperature for five minutes, 3-methylcyclopentadecan-1,5-dione (II-1) (3.0 g, purity: 100%, 11.9 mmol) was added thereto. The flask was heated to 100° C. in an oil bath, and the reaction was carried out under heating and reflux for six hours to obtain a reaction mixture containing 14-methyl-16-oxabicyclo[10.3.1]hexadec-12-ene (I-1). As a result of the GC analysis of the reaction mixture, the raw material conversion rate was 6%, and the reaction selectivity was 100%.

Example 6

The same procedure as in Example 5 was carried out except that isopropanol was changed to 2-butanol, and the temperature was changed from 100° C. to 120° C. As a result of the GC analysis of the reaction mixture, the raw material conversion rate was 20%, and the reaction selectivity was 99%.

Example 7

The same procedure as in Example 5 was carried out except that isopropanol was changed to cyclohexanol, and the temperature was changed from 100° C. to 180° C. As a result of the GC analysis of the reaction mixture, the raw material conversion rate was 55%, and the reaction selectivity was 99%.

Example 8

In a 30 ml two-necked flask to which a septum and a Dean-Stark tube with a Dimroth were attached, 85% zirconium n-butoxide (536 mg, 1.19 mmol, 0.10 eq.), ethylene glycol (74 mg, 1.19 mmol, 0.10 eq.), trifluoroacetic acid (272 mg, 1.19 mmol, 0.20 eq.), and cyclohexanol (10 g, 9.98 mmol, 8.40 eq.) were placed. After stirring the mixture in the flask at room temperature for 30 minutes, 3-methylcyclopentadecan-1,5-dione (II-1) (3.0 g, purity: 100%, 11.9 mmol) was added thereto. The flask was heated to 180° C. in an oil bath, and the reaction was carried out under heating and reflux for seven hours to obtain a reaction mixture containing 14-methyl-16-oxabicyclo[10.3.1]hexadec-12-ene (I-1). As a result of the GC analysis of the reaction mixture, the raw material conversion rate was 92%, and the reaction selectivity was 97%.

Example 9

In a 500 ml three-necked flask to which a septum, a nitrogen inlet, and a rectification column (10-stage Sulzer laboratory packing column) were attached, cyclohexanol (60 g, 595 mmol, 1.00 eq.) was placed, and subsequently 85% zirconium n-butoxide (13.4 g, 29 mmol, 0.05 eq.), ethylene glycol (1.85 g, 29 mmol, 0.05 eq.), and trifluoroacetic acid (3.40 g, 29 mmol, 0.05 eq) were added in this order. After stirring the mixture in the flask at room temperature for five minutes, 3-methylcyclopentadecan-1,5-dione (II-1) (150 g, purity: 100%, 595 mmol) was added thereto. The flask was heated to 180° C. in an oil bath, and the reaction was carried out at a reflux ratio of 40:1. Five hours after the start of the reaction, cyclohexanol (30 g, 298 mmol) was added to the reaction mixture. The reaction was carried out for four more hours to obtain a reaction mixture containing 14-methyl-16-oxabicyclo[10.3.1]hexadec-12-ene (I-1). As a result of the QC analysis of the reaction mixture, the raw material conversion rate was 96%, and the reaction selectivity was 99%.

Example 10

In a 200 ml three-necked flask to which a thermometer, a septum, a KIRIYAMA Pac (FR64-4-C, column inner diameter: 16 mm, number of theoretical stages: 10 stages), a KIRIYAMA small fractionating head, a fractionator, and a distillate receiver were attached, cyclohexanol (30.9 g, Wako Pure Chemical Industries, Ltd., 308 mmol, 5.00 eq), 85% zirconium n-butoxide (2.78 g, Wako, 6.16 mmol, 0.10 eq), and 3-methylcyclopentadecan-1,6-dione (II-1) (30.0 g, purity: 51.8%, 61.6 mmol) prepared by the method described in Production Example 1 were placed. The flask was heated in an ail bath under a nitrogen atmosphere, and the reaction was carried out for 16 hours at an in-bath temperature of 175° C. and a reflux ratio of 80:2. After completion of the reaction, the reaction mixture was cooled and transferred to a 200 ml three-necked pear-shaped flask. A capillary tube, a thermometer, a KIRIYAMA Pac (FR64-4-C, column inner diameter: 16 mm, number of theoretical stages: 10 stages), a KIRIYAMA small fractionating head, a fractionator, and a distillate receiver were attached to the flask. The pressure inside the flask was reduced to 1.0 torr using a vacuum pump and a pressure regulator while blowing nitrogen from the capillary tube. Then, the reflux ratio was set to 20:1, and the reaction mixture was rectified while raising the internal temperature stepwise from room temperature to 180° C. using an oil bath. The distillate was collected in several fractions, and each fraction was analyzed by gas chromatography. After distillation stopped, depressurization was released after cooling, and the operation was stripped. As a result of the GC analysis of each fraction, the raw material conversion rate was 90%, and the reaction selectivity was 95%.

Example 11

In a 200 ml throe-necked flask to which a thermometer, a septum, a KIRIYAMA Pile (FR64-4-C, column inner diameter: 16 mm, number of theoretical stages: 10 stages), a KIRIYAMA small fractionating head, a fractionator, and a distillate receiver wore attached, 2-octanol (38.9 g, TCI, 293 mmol, 5.00 eq.), 85% zirconium n-butoxide (2.69 g, 5.97 mmol, 0.10 eq.), and 3-methylcyclopentadecan-1,5-dione (II-1) (29.1 g, purity-51.8%, 59.7 mmol) prepared by the method described in Production Example 1 were added. The flask was heated in an oil bath under a nitrogen atmosphere, and the reaction was carried out for 14.5 hours at an in-hath temperature of 190° C. and a reflux ratio of 80:2. After completion of the reaction, the reaction mixture was cooled and transferred to a 200 ml three-necked pear-shaped flask. A capillary tube, a thermometer, a KIRIYAMA Pac (FR64-4-C, column inner diameter: 16 mm, number of theoretical stages: 10 stages), a KIRIYAMA small fractionating head, a fractionator and a distillate receiver were attached to the flask. The pressure inside the flask was reduced to 1.0 torr using a vacuum pump and a pressure regulator while blowing nitrogen from the capillary tube. Then, the reflux ratio was set to 20:1, and the reaction mixture was rectified while raising the internal temperature stepwise from room temperature to 180° C. using an oil bath. The distillate was collected in several fractions, and each fraction was analyzed by gas chromatography. After distillation stopped, depressurization was released after cooling, and the operation was stopped. As a result of the GC analysis of each fraction, the raw material conversion rate was 99%, and the reaction selectivity was 85%.

Tables 1 and 2 below summarize the contents of the examples.

TABLE 1

(Purity of raw material: all 100%)

| Example No. | Kind of metal catalyst | | Alcohol Kind | Additive Kind | Reaction time Time | Yield of compound (I-1) | |
| --- | --- | --- | --- | --- | --- | --- | --- |
| | Kind | Equivalent (relative to compound (II-1)) | | | | Conversion rate (%) | Selectivity (%) |
| 1 | Al(O₁Pr)3 | 105 mol % | Isopropanol | — | 8 hours | 100 | 20 |
| 2 | Al(O₁Pr)3 | 105 mol % | Isopropanol | TFA | After confirmation of the disappearance of raw material | 100 | 83 |
| 3 | ZrO₂ | 102 mol % | Isopropanol | TFA | 5 days | 11 | 24 |
| 4 | ZrO₂ | 102 mol % | Cyclohexanol | TFA | 3 days | 92 | 72 |
| 5 | Zr(OnBu)4 | 10 mol % | Isopropanol | TFA | 6 hours | 6 | 100 |
| 6 | Zr(OnBu)4 | 10 mol % | 2-Butanol | TFA | 6 hours | 20 | 99 |
| 7 | Zr(OnBu)4 | 10 mol % | Cyclohexanol | TFA | 6 hours | 55 | 99 |
| 8 | Zr(OnBu)4 | 10 mol % | Cyclohexanol | TFA, EG | 7 hours | 92 | 97 |
| 9 | Zr(OnBu)4 | 5 mol % | Cyclohexanol | TFA, EG | 9 hours | 95 | 99 |

TABLE 2

(Purity of raw material: all 100%)

| Example No. | Purity of raw material % by weight | Kind of metal catalyst | | Alcohol Kind | Reaction time Hour | Yield of compound (I-1) | |
| --- | --- | --- | --- | --- | --- | --- | --- |
| | | Kind | Equivalent (relative to compound (II-1)) | | | Conversion rate (%) | Selectivity (%) |
| 10 | 51.8% | Zr(OnBu)4 | 10 mol % | Cyclohexanol | 16 hours | 90 | 95 |
| 11 | 51.8% | Zr(OnBu)4 | 10 mol % | 2-Octanol | 14.5 hours | 99 | 85 |

Tables 1 and 2 indicate that the method of the present invention can provide the compound of formula (I) in one step from the compound of formula (II). Moreover, Table 1 indicates that not only high selectivity but also high conversion rate can be obtained depending on the kind of the metal catalyst to be used.

The production method of the present invention can provide end ether in one step from the diketone in the presence of u specific metal catalyst and a specific alcohol.

The invention claimed is:

1. A method for producing a compound represented by general formula (I), the method comprising:
reacting a compound represented by general formula (II) in the presence of a metal catalyst comprising at least one metal element selected from the group consisting of aluminum, zirconium, and titanium, and an alcohol comprising at least one selected from the group consisting of a primary alcohol and a secondary alcohol to obtain the compound represented by general formula (I),

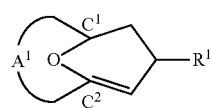
(I)

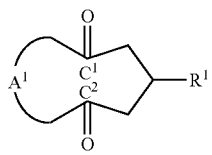
(II)

wherein the group -$A^1$- (where the front bond denotes a bond that bonds with a carbon atom $C^1$ while the back bond denotes a bond that bonds with a carbon atom $C^2$ is an alkylene group with 4 or more and 16 or less of carbon atoms that may optionally contain a hetero atom and that may optionally have a substituent, and
$R^1$ is hydrogen or an alkyl group with 1 or more and 6 or less of carbon atoms.

2. The method according to claim 1, wherein the metal catalyst is at least one selected from the group consisting of aluminum alkoxide, zirconium alkoxide, and titanium alkoxide.

3. The method according to claim 1, wherein the group -$A^1$- is an alkylene group with 6 or more and 14 or less of carbon atoms.

4. The method according to claim 1, wherein $R^1$ is an alkyl group with 1 or more and 3 or less of carbon atoms.

5. The method according to claim 1, wherein the alcohol comprises a secondary alcohol.

6. The method according to claim 1, wherein the alcohol has a boiling point of 100° C. or higher.

7. The method according to claim 1, wherein the secondary alcohol is cyclohexanol or 2-octanol.

8. The method according to claim 1, wherein the reacting is performed at a temperature of 100° C. or higher and 250° C. or lower.

9. The method according to claim 1, wherein a mole ratio of the compound of formula (II) to the alcohol (compound of formula (II): alcohol) is 1:1 to 1:50.

10. The method according to claim 1,
wherein a mole ratio of the compound of formula (II) to the metal catalyst (compound of formula (II): metal catalyst) is 1:0.01 to 1:1.2 when the metal catalyst is a metal catalyst comprising zirconium, and
a mole ratio of the compound of formula (II) to the metal catalyst (compound of formula (II) : metal catalyst) is 1:0.5 to 1:1.5 when the metal catalyst is a metal catalyst comprising at least one metal element selected from the group consisting of aluminum and titanium.

11. The method according to claim 1, wherein the reacting the compound of general formula (II) in the presence of the metal catalyst and the alcohol to obtain the compound of general formula (I) is carried out in the presence of at least one additive selected from an acid and a diol.

12. The method according to claim 11, wherein the acid is trifluoroacetic acid, and the diol is ethylene glycol.

13. A method for producing a compound represented by general formula (III), the method comprising:
   reacting a compound represented by general formula (II) in the presence of a metal catalyst comprising at least one metal element selected from the group consisting of aluminum, zirconium and titanium, and an alcohol comprising at least one selected from the group consisting of a primary alcohol and a secondary alcohol to obtain a compound represented by general formula (I); and
   decyclizing the resultant compound represented by general formula (I) to obtain the compound represented by general formula (III),

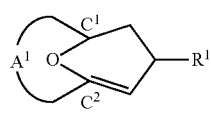 (I)

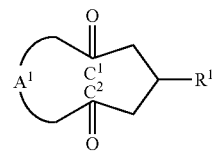 (II)

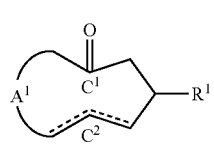 (III)

wherein the group -$A^1$- (where the front bond denotes a bond that bonds with a carbon atom $C^1$ while the back bond denotes a bond that bonds with a carbon atom $C^2$ is an alkylene group with 4 or more and 16 or less of carbon atoms that may optionally contain a hetero atom and that may optionally have a substituent, and $R^1$ is hydrogen or an alkylene group with 1 or more and 6 or less of carbon atoms.

* * * * *